(12) United States Patent
Kikuchi et al.

(10) Patent No.: US 6,488,682 B2
(45) Date of Patent: Dec. 3, 2002

(54) SPINAL IMPLANT, DRIVER TOOL AND NUT GUIDE

(75) Inventors: Shinichi Kikuchi, Fukushima (JP); Shinichi Konno, Fukushima (JP); Kazuya Oribe, Tokyo (JP); Hiroshi Takamido, Nagoya (JP); Noriyuki Ina, Toyohashi (JP)

(73) Assignee: Showa Ika Kohgyo Co., Ltd., Aichi-ken (JP)

( * ) Notice: Subject to any disclaimer, the term of this patent is extended or adjusted under 35 U.S.C. 154(b) by 0 days.

(21) Appl. No.: 09/818,229

(22) Filed: Mar. 27, 2001

(65) Prior Publication Data

US 2001/0029374 A1 Oct. 11, 2001

(30) Foreign Application Priority Data

| Mar. 28, 2000 | (JP) | ........................... 2000-089786 |
| Mar. 31, 2000 | (JP) | ........................... 2000-099192 |
| May 10, 2000 | (JP) | ........................... 2000-137275 |

(51) Int. Cl.[7] ............................................. A61B 17/56
(52) U.S. Cl. ............................. 606/61; 606/72; 606/73; 623/17.11
(58) Field of Search ................ 606/60, 61, 69, 606/70, 71, 72, 73; 623/17.11, 17.15, 17.16

(56) References Cited

U.S. PATENT DOCUMENTS

| 5,154,719 A |   | 10/1992 | Cotrel |
| 5,496,321 A | * | 3/1996 | Puno et al. |
| 5,536,268 A | * | 7/1996 | Griss |
| 5,658,285 A | * | 8/1997 | Marnay et al. |
| 5,879,351 A |   | 3/1999 | Viart |
| 5,910,142 A | * | 6/1999 | Tatar |
| 5,984,923 A | * | 11/1999 | Breard |
| 6,019,760 A | * | 2/2000 | Metz-Stavenhagen et al. |

FOREIGN PATENT DOCUMENTS

| JP | 6-38977 | 2/1990 |
| JP | 11-318932 | 11/1999 |

* cited by examiner

Primary Examiner—Pedro Philogene
(74) Attorney, Agent, or Firm—Greenblum & Bernstein, P.L.C.

(57) ABSTRACT

A spinal implant for an osteosynthesis device has a vertebral connecting rod for interconnecting adjacent vertebral bodies and comprises an implant body including a head section having a threaded portion, a rod retaining recess opening outward for retaining the connecting rod therein and a slanted engagement surface formed on a bottom wall of the rod retaining recess. The spinal implant further includes a nut member and a rod movement stabilizing device to preserve mobility to the connecting rod.

11 Claims, 13 Drawing Sheets

SPINAL IMPLANT, DRIVER TOOL AND NUT GUIDE

BACKGROUND OF THE INVENTION

The present invention relates to spinal implants for osteosynthesis devices and, more particularly, to a spinal implant, a driver tool specifically suited for the spinal implant, and a nut guide suited for the spinal implant.

In recent years, various research and development have been attempted to provide a spinal implant that is designed to achieve adaptation to differences in alignment, augulation and depth of penetration of adjacent spinal implants anchored to vertebral bodies which are spaced from one another.

One of such implants is disclosed in U.S. Pat. No. 5,154,719. This device includes a head portion having a pair of upright branches which are internally threaded and which has a U-shaped recess, and a screw portion projecting from the head portion. A connecting rod is received in the two branches, which are fixed in place by means of a ring member. During this operating step, there exist some difficulties in precisely adjusting the orientation of the U-shaped recesses of the spaced spinal implants anchored in vertebral bodies, angulation of the spinal implants and depth of the spinal implants, with a resultant undesirable fixation of the implants and the connecting rod. Since, further, the screw portion is composed of a solid material and the screw portion is merely anchored in the vertebral body. Accordingly, after the spinal implant penetrates in the vertebral body, fixation of the spinal implant is unstable and is liable to be undesirably affected with external forces when they are applied to the spinal implants.

U.S. Pat. No. 5,879,351 discloses a spinal osteosynthesis device comprising at least one vertebral rod, pedicle screws and deformable connectors. In this prior art, each of the pedicle screws is composed of the same solid material as in the prior art discussed above, and a difficulty is similarly encountered in reliably fixing the pedicle screw in the vertebral body. Further, each of the deformable connectors has an oblong opening through which a head portion of the screw extends and each connector is resiliently supported between a cylindrical base and a nut, with a given space being provided for permitting relative movement of the vertebral rod. With such a structure, the spinal implant is caused to have a large number of component parts, resulting in a complicated structure and an increased cost.

In known techniques, it has been a usual practice to lock a plug into the spinal implant by means of a tool holder. In practice, there are two types of head section formed with two upright branches, that is, a first type of head section having an internally formed thread, and a second type of head section having an outwardly formed thread. In the first type, the plug is screwed in the internal thread of the head section. In this event, the two branches are loosened, thereby providing a difficulty in tightly locking the connecting rod in the spinal implant. On the contrary, in the second type, the plug is screwed onto the outer thread of the head section. In this event, an outer periphery of the plug has a hexagonal profile, and a driver tool having a hexagonal groove is brought into engagement with the outer hexagonal wall of the plug for rotating the plug. In this event, since the driver tool has an outer diameter larger than that of the plug, increasing an occupying space for rotating the driver tool. Under these conditions, when two spinal implants are anchored in adjacent vertebral bodies in a relationship closer to one another, the outer periphery of the driver tool is liable to interfere with the adjacent plug of the spinal implant, causing difficulties in rotating operation of the driver tool.

SUMMARY OF THE INVENTION

The present invention has been made with a view to overcoming the various disadvantages encountered in prior art devices and it is therefore an object of the present invention to provide a spinal implant for an osteosynthesis device, a driver tool for rotating the spinal implant, and a nut guide for guiding the implant body and the driver tool.

According to a first aspect of the present invention, there is provided a spinal implant for an osteosynthesis device having a vertebral connecting rod for interconnecting vertebral bodies spaced from one another. The spinal implant comprises an implant body including a head section having a threaded portion and a rod retaining recess opening outward for retaining the connecting rod therein, and an anchoring screw section longitudinally extending from the head section and adapted to be screwed into the vertebral body, a retaining plug coupled to the head section of the implant body to maintain the connecting rod in place, and rod movement stabilizing means directly located in at least one of the rod retaining recess and the retaining plug for allowing pivotal movement of the connecting rod in the retaining recess, thereby preserving mobility to the connecting rod.

According to a second aspect of the present invention, there is provided a driver tool for a spinal implant having an implant body and an anchoring screw portion, and a nut member screwed onto a head portion of the implant body and having an upper wall formed with a tool engagement groove. The driver tool comprises an elongated shaft, and a tubular tool end having substantially the same diameter as that of the nut member, the tubular tool end having an engaging segment adapted to engage with the engagement groove formed on the upper wall of the nut member.

According to a third aspect of the present invention, there is provided a nut guide for guiding a nut member of a spinal implant having an implant body and an anchoring screw section, and for guiding a driver tool having a lower end formed with a nut engagement tip, wherein a vertebral connecting rod is retained with a pair of the spinal implant to be anchored into vertebral bodies. The nut guide comprises a grip section, and a hollow cylindrical shaft extending from the grip section and adapted to permit insertion of the driver tool therein, the cylindrical shaft having a lower distal end formed with a rod engaging segment for engaging with and retaining the connecting rod to place the lower distal end in a fixed place, and a threaded bore formed rearward of the rod engaging segment for momentarily receiving the nut member therein. The cylindrical shaft allows the driver tool to pass therein such that the nut engagement tip is brought into engagement with the nut member guided with the cylindrical shaft to move the nut member from the threaded bore to the implant body of the spinal body.

Other aspect and advantages of the invention will become more apparent from the following description, taken in conjunction with the accompanying drawings, illustrating by way of example the principles of the invention.

DETAILED DESCRIPTION OF THE PREFERRED EMBODIMENTS

Figure 1:
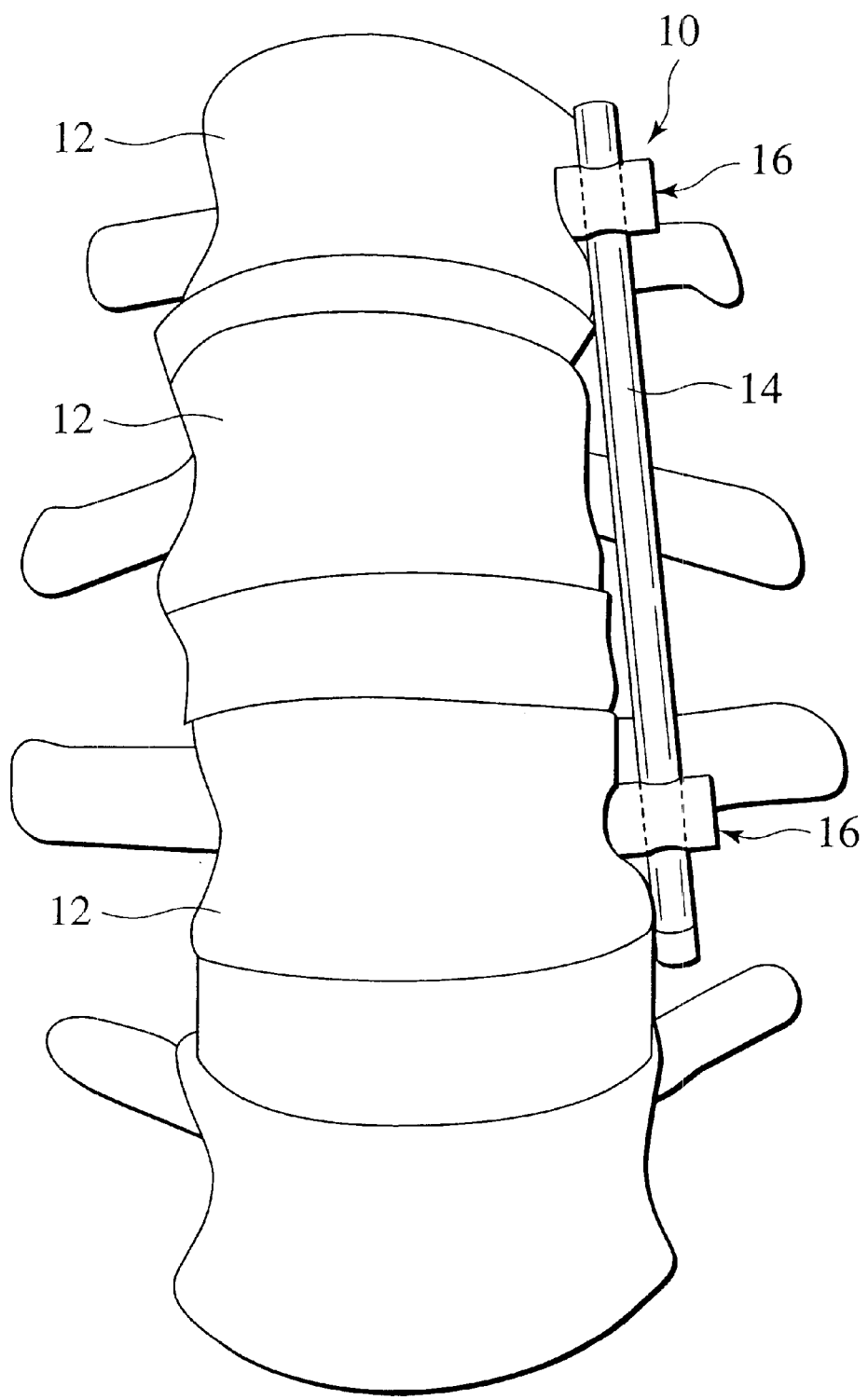
FIG. 1 is a schematic view of an osteosynthesis device incorporating a first preferred embodiment of a spinal implant according to the present invention, with a connecting rod being utilized to interconnect spaced vertebral bodies by means of plural spinal implants.
Figure 2:
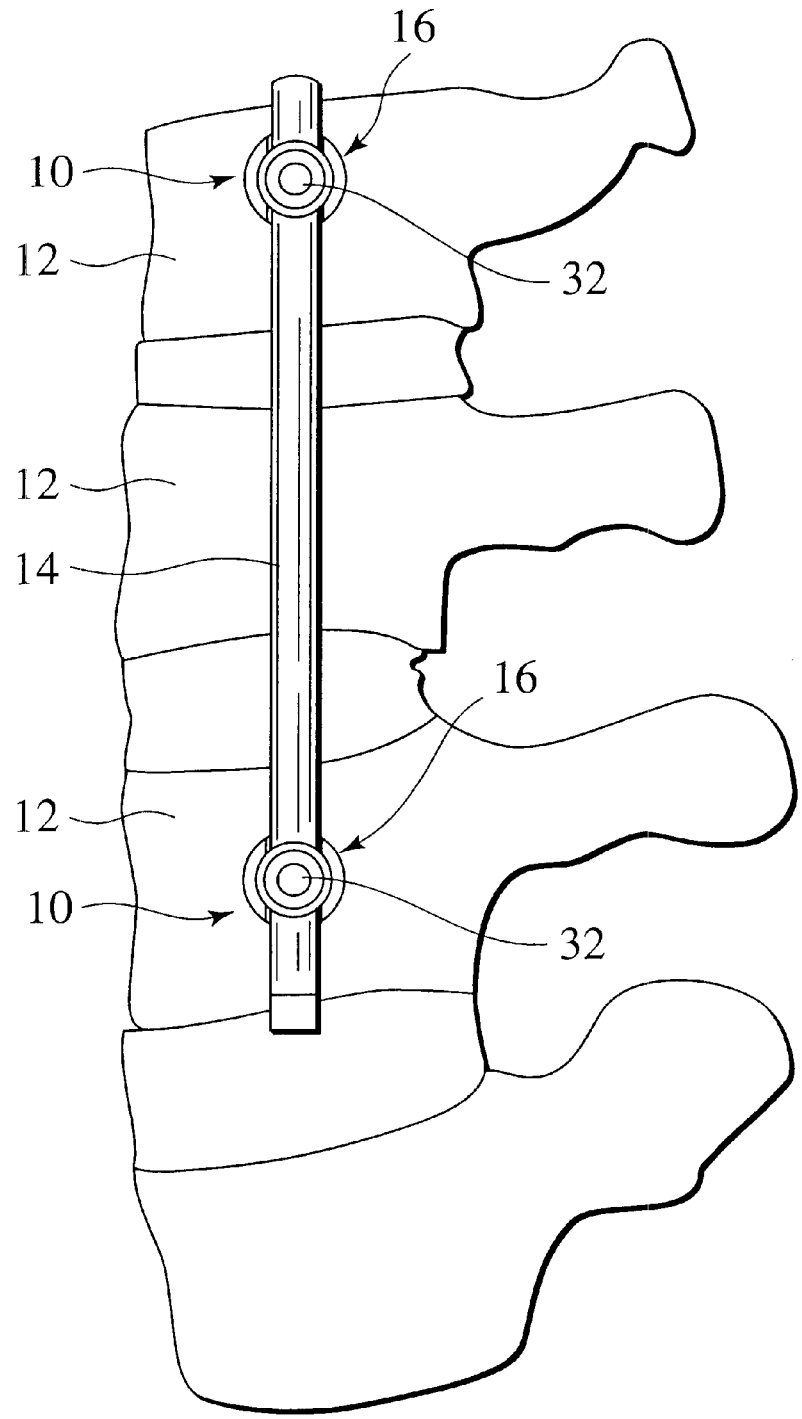
FIG. 2 is a side view illustrating the relationship between the plural spinal implants and the associated connecting rod.

Referring to the drawings and more particularly to FIGS. 1 and 2, a spinal osteosynthesis device, generally designated at 10, is shown as applied to separate vertebral bodies 12 for interconnecting plural vertebral bodies 12 in place.

The spinal osteosynthesis device 10 includes an elongated vertebral connecting rod 14 retained by a pair of spinal implants 16 of a first preferred embodiment according to the present invention. Each of the spinal implants 16 penetrates each vertebral body 12 in a manner as will be discussed below in detail. The connecting rod 14 is made of malleable, elastically deformable material having a large elastic capacity, permitting elastic deformation necessary for adaptation it to differences in alignment, angulation and depth of penetration of the implants 16.

Figure 3:
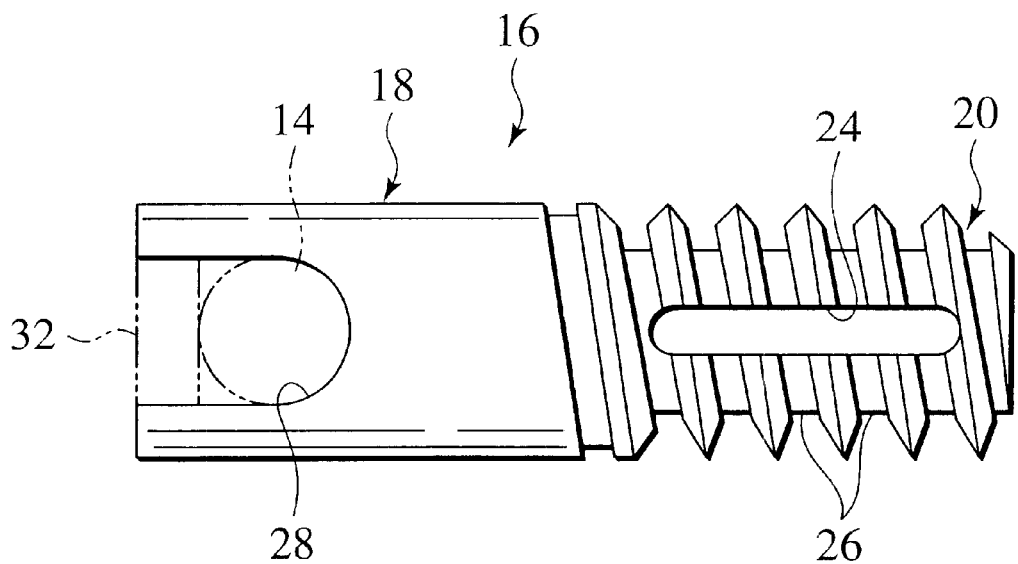
FIG. 3 is an enlarged front view of the first preferred embodiment of the spinal implant according to the present invention.
Figure 4:
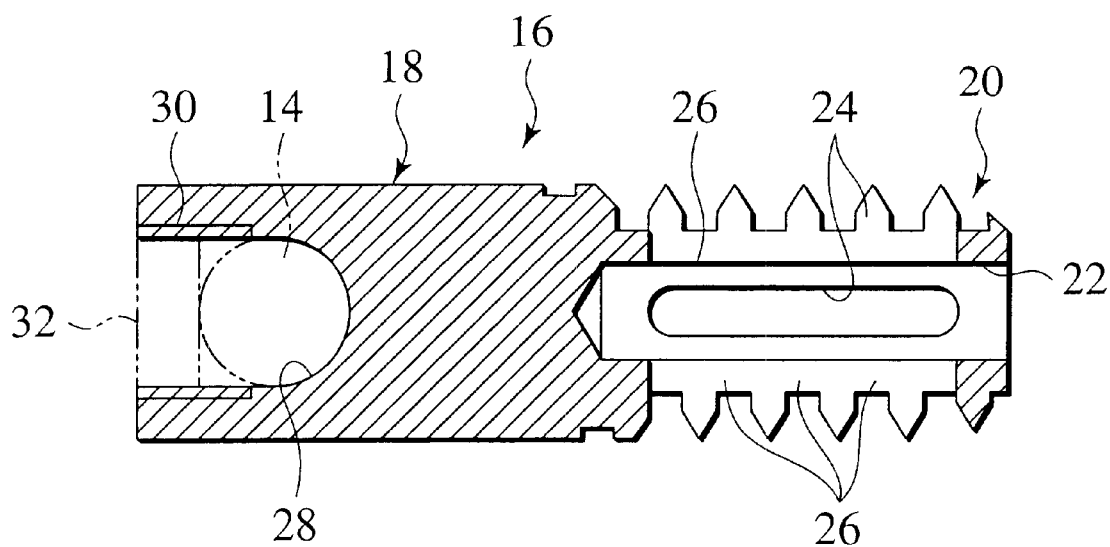
FIG. 4 is a cross sectional view of the spinal implant shown in FIG. 3.

Referring now to FIGS. 3 and 4, the spinal implant 16 includes a cylindrical implant body 18 for firmly retaining the connecting rod 14 in place, and an anchoring screw section 20 that longitudinally extends from the implant body 18 and adapted to be anchored in the vertebral body 12 (see FIGS. 1 and 2).

The anchoring screw section 20 has a hollow internal fusion chamber 22, and a plurality of spinal openings 24 each of which is composed of a longitudinally extending elongated slit. Each of the elongated slit 24 transversely extends through the anchoring screw section 20 from one side to the other side and communicates with the internal fusion chamber 22 to permit borne ingrowth into the fusion chamber 22. Thus, the anchoring screw section 20 has a plurality of circumferentially spaced, elongated wall segments 26 defined between the hollow internal fusion chamber 22 and the plural slits 24, providing elastic deformation to the anchoring screw section 20 to allow adaptation of any positioning of the threaded section while permitting an effective fixation without impairing the borne anchorage.

A head portion of the implant body 18 is formed with a U-shaped rod retaining recess 28 that opens outward, and an internally threaded bore 30 extending in a longitudinal direction at a position adjacent the rod retaining recess 28. A disc shaped nut member 32 is screwed into the internally threaded bore 30, thereby retaining the connecting rod 14 in place in the rod retaining recess 28.

Figure 5:
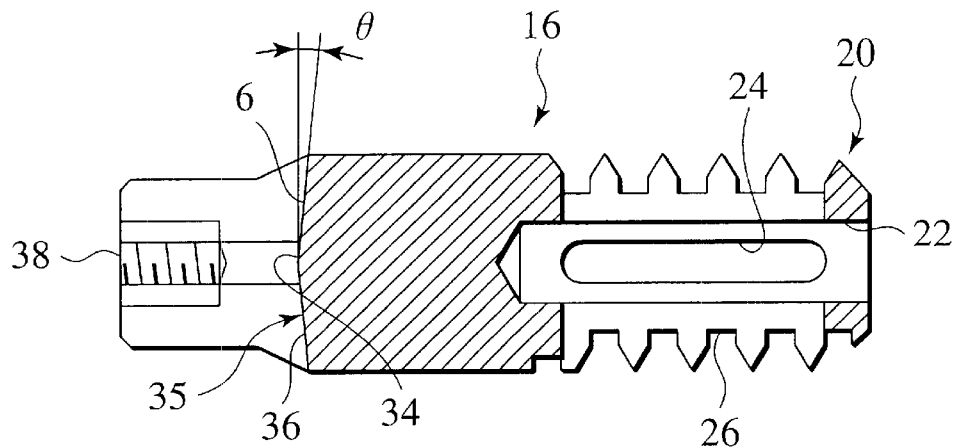
FIG. 5 is another cross sectional view of the spinal implant shown in FIG. 3.
Figure 6:
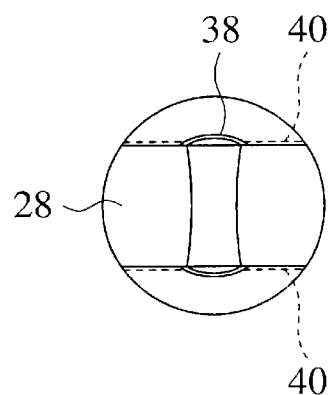
FIG. 6 is a left side view of the spinal implant shown in FIG. 3.

As seen in FIGS. 5 and 6, a bottom wall 34 of the retaining recess 28 includes a rod movement stabilizing means 35 composed of slanted engagement surfaces 36 directly located in the rod retaining recess 28 for allowing pivotal movement of the connecting rod 14 in the retaining recess 28, thereby preserving mobility to the connecting rod 14. To this end, each of the slanted engagement surface 36 is slightly inclined from points slightly displaced from the center of axis of the implant body 18 at an angle Θ from an axis of the connecting rod 14 perpendicular to the axis of the implant body 18.

With such a structure, the connecting rod 14 is allowed for pivotal movement within a range defined by the slanted engagement surfaces 36 of the retaining recess 28 of the implant body 18. Thus, the slanted engagement surfaces 36 of the rod movement stabilizing means 35 is defined in the retaining recess 28 of the implant body 18, allowing the connecting rod 14 to be inclined.

Although, the connecting rod 14 is inclined in a plane involving the center of axis of the implant body 18, the slanted engagement surface 36 of the rod movement stabilizing means 35 may be modified such that the connecting rod 14 is allowed to be slightly inclined in a plane crossing the central axis of the implant body 18. More particularly, as shown by a phantom line in FIG. 6, the retaining recess 28 has inclined engagement surfaces 40 formed in a longitudinal direction in right and left directions in FIG. 6, except for the threaded portion 38.

With the structure discussed above, the plural spinal implants 16 are screwed into and anchored in separate vertebral bodies 12 in a manner as shown in FIGS. 1 and 2 such that the associated rod retaining sections 28 of two implant bodies 18 are aligned, and both ends of the connecting rod 14 are received in the implant bodies 18. In a subsequent step, the nut member 32 are screwed into the threaded portions 30 of the implant bodies 18, respectively, firmly retaining the both ends of the connecting rod 14 to clamp the same in the required position.

Due to the separate elongated wall segments 26 formed in the anchoring screw section 20, the anchoring screw section 20 is allowed to be penetrated into the vertebral body 12 in reduced diametrical size owing to the inward elastic deformation of the separate elongated segments 26, thereby providing ease of penetration of the implant 16. Since, also, when the penetration of the anchoring screw section 20 has been completed, the separate elongated wall segments 26 expand to their original position due to their restoring forces, thereby providing an improved fixation, in an early stage, of the screw section 20 to the vertebral body 12 in a highly reliable manner. Owing to the provision of the plurality of spinal openings defined by the elongated slits 24 and the hollow internal fusion chamber 22, further, the spinal implant 16 permits borne ingrowth into the hollow fusion chamber 22 for thereby further improving fixation of the implant.

In a event the both ends of the connecting rod 14 are fitted to the retaining recesses 28 of the implant bodies 18 after the plural spinal implants 16 are firmly fitted to the vertebral bodies 12 in a manner discussed above, if the rotational positions of the retaining recesses 28 of the plural spinal implants 16 are not aligned with one another, a desired one of the spinal implants 16 may be slightly rotated. In addition, further, when the depths of penetration of the plural spinal implants 16 are different from one another and the plural spinal implants 16 undergo misalignment in height, the connecting rod 14 is partly allowed to be suitably deformed along the slanted surface 36, absorbing a slight difference in height of the bottom walls of the plural spinal implants 16 penetrated in the vertebral bodies 12.

In other words, even when there exists a slight difference in height between the bottom walls 34 of the adjacent spinal implants 16, the connecting rod 14 is reliably adaptable to that difference, providing improved engagement of the connecting rod in the plural spinal implants in an easy and simplified manner.

Figure 7:
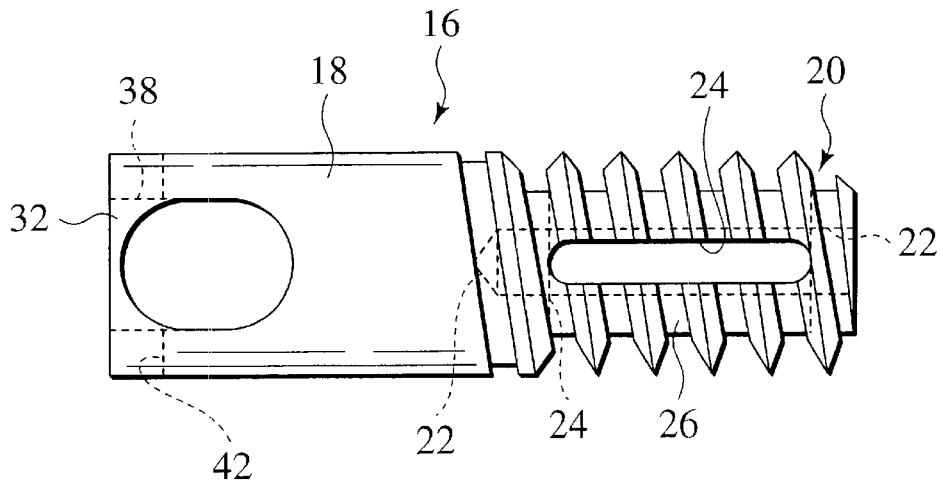
FIG. 7 is an enlarged front view of a second preferred embodiment of a spinal implant according to the present invention.

FIG. 7 shows a second preferred embodiment of a spinal implant according to the present invention, with like parts bearing the same reference numerals as those used in FIGS. 1 to 5.

The spinal implant 16 of FIG. 7 differs in structure from the first preferred embodiment of the spinal implant in that the implant body 18 has a rod retaining recess 40 composed of a longitudinally extending oblong opening and a distal end of the implant body 18 has a laterally extending tool engagement groove 42. The spinal implant 16 of the second preferred embodiment has the same advantages as those of the first preferred embodiment discussed above. Other features of the second preferred embodiment of the spinal implant 16 are identical to those of the first preferred embodiment and, accordingly, a detailed description of the second preferred embodiment of the spinal implant 16 is herein omitted for the sake of simplicity.

Figure 8:
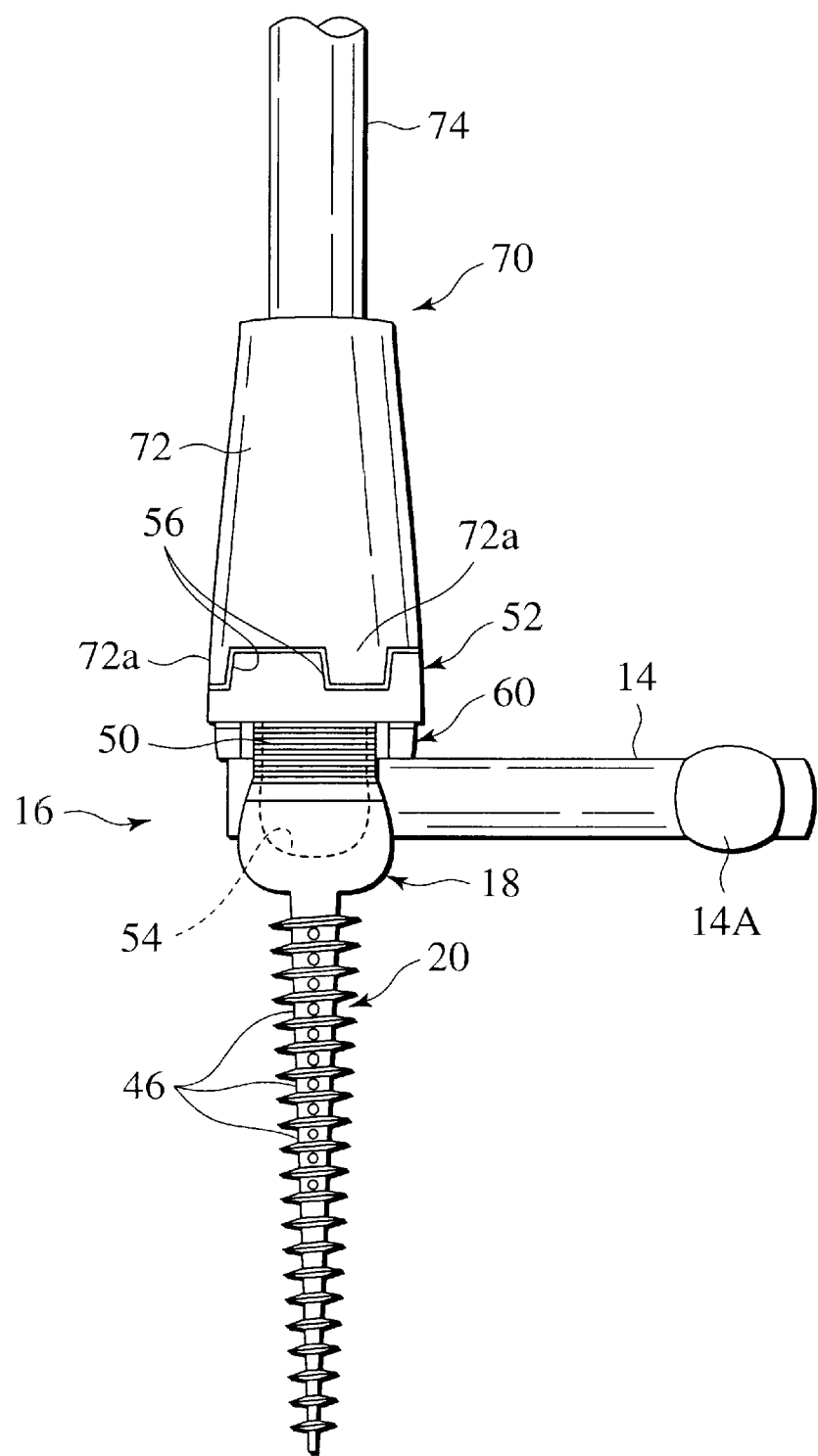
FIG. 8 is an enlarged front view of a third preferred embodiment of a spinal implant according to the present invention, with the connecting rod being shown as being fastened by the spinal implant of the third preferred embodiment.

FIGS. 8 to 11 show a third preferred embodiment of a spinal implant according to the present invention. In FIG. 8, the spinal implant 16 includes an implant body 18 and an anchoring screw section 20 having a plurality of small apertures 46 extending in a plane perpendicular to the axis of the screw portion 20 to allow borne ingrowth therein. The implant body 18 has an upper end formed with an outer thread 50, to which a nut member 52 having an upper wall formed with tool engagement grooves 56 is screwed. The implant body 18 also has a U-shaped retaining recess 54, with which a spherical engaging segment 14a of a connecting rod 14 engages for pivotal movement.

Figure 10:
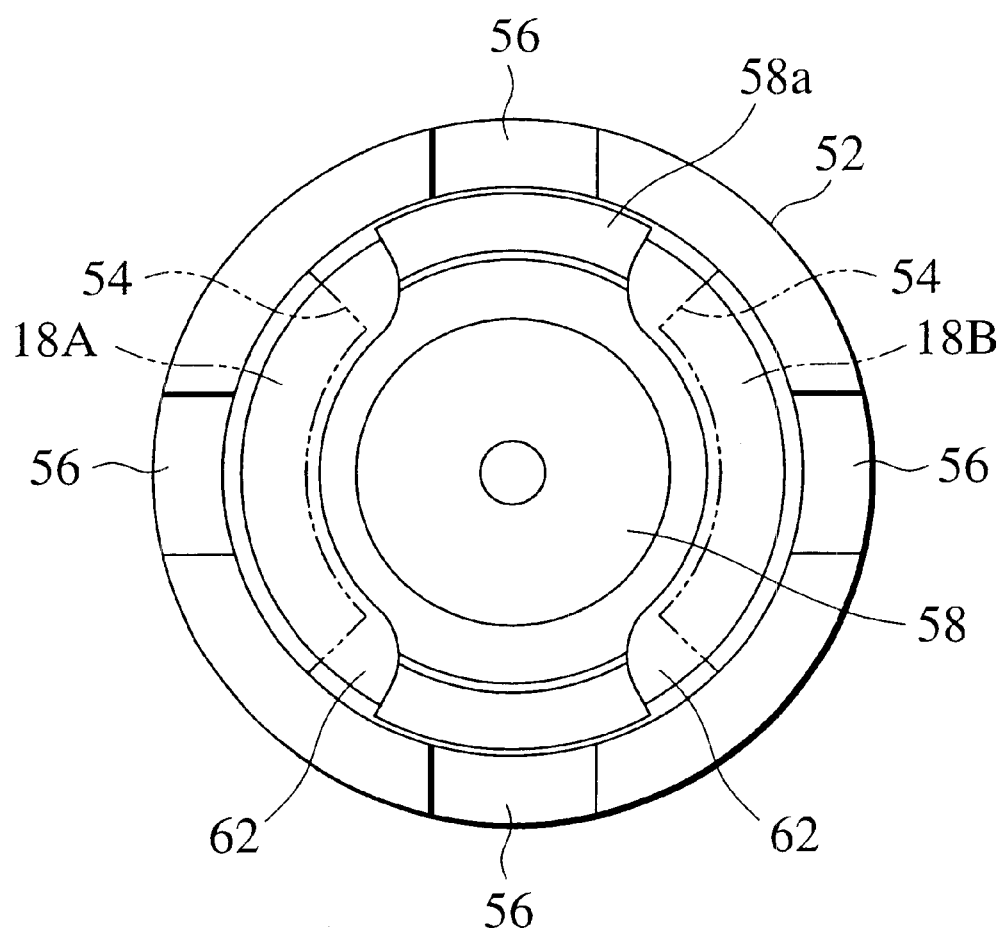
FIG. 10 is an enlarged, plan view of the nut member shown in FIG. 8.
Figure 11:
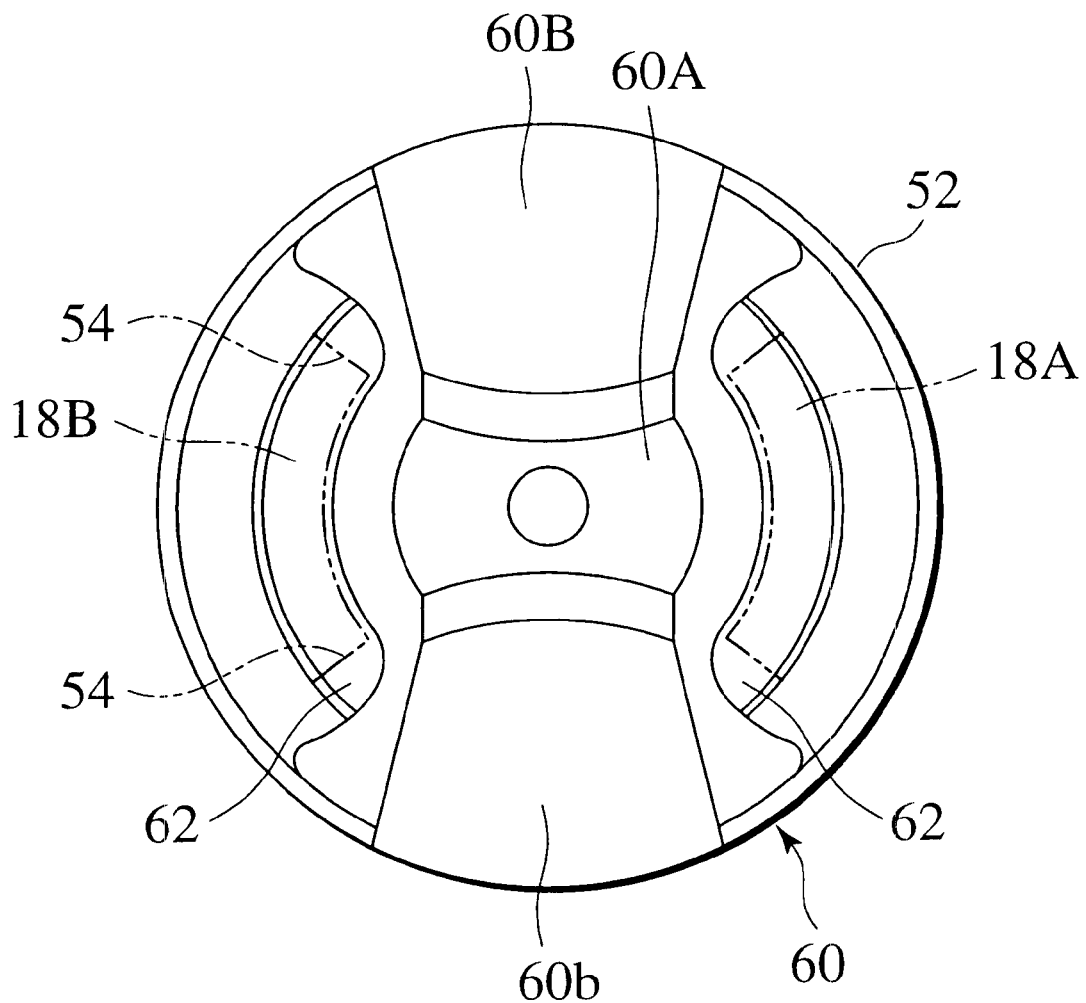
FIG. 11 is an enlarged, bottom view of the nut member shown in FIG. 8.

As best seen in FIG. 10, the implant body 18 has a pair of upright retaining segments 18A, 18B providing relatively large spaces 62 and each having an arch-shaped cross section. Thus, the upright retaining segments 18A, 18B provide an open distal end such that when the spherical engaging segment 14A is retained in the U-shaped recess 54, the connecting rod 14 is allowed for pivotal movement relative to the central axis of the spinal implant 16.

Figure 9:
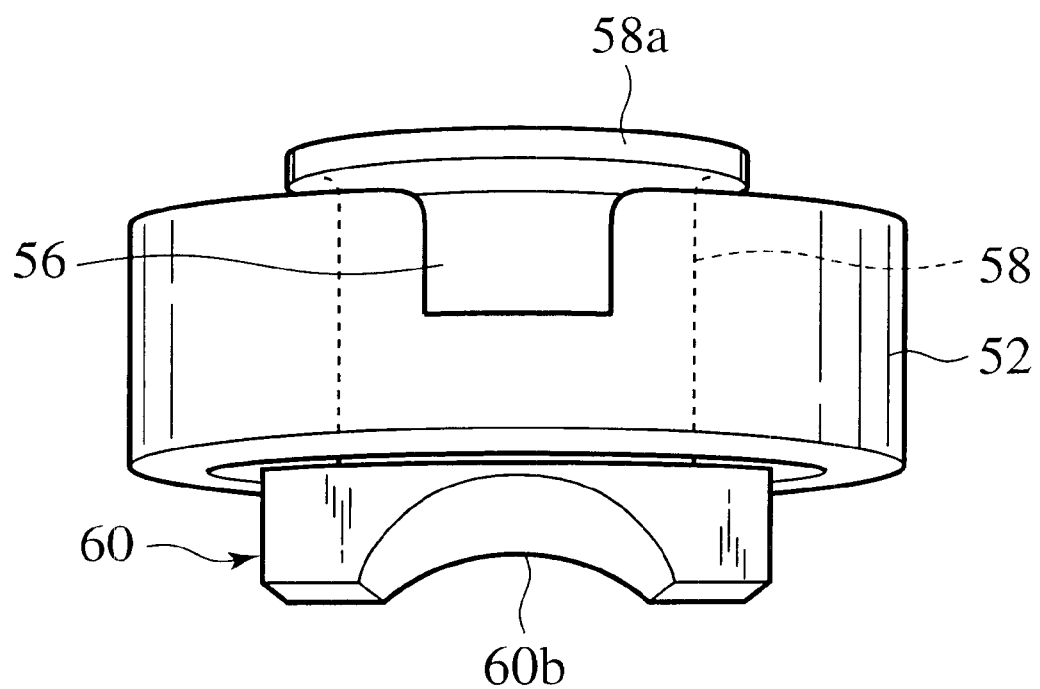
FIG. 9 is an enlarged, front view of a nut member forming part of the spinal implant shown in FIG. 8.

The nut member 52 has a ring-shape having an inner thread engaging the outer thread 50 of the implant body 18. An upper side of the nut member 52 has a plurality of tool engagement grooves 56 that cross each other in lateral direction. As best seen in FIGS. 9 and 10, the ring-shape nut member 52 receives therein a central pivot shaft 58 coaxially extending through the nut member 52. A lower ends of the central pivot shaft 58 is integrally formed with a rod retaining member 60, that includes a central, globular retaining groove 60a, and a pair of laterally extending arch-shaped retaining grooves 60b. As seen in FIG. 9, the rod retaining member 60 projects downward from a lower distal end of the nut member 52. The rod retaining member 60 has a radial length substantially equal to the diameter of the nut member 52 and has a lateral width slightly smaller than the width of the rod retaining groove 54. An upper end of the central pivot shaft 58 has a circular flange 58a having substantially the same shape as the rod retaining member 60.

Figure 12:
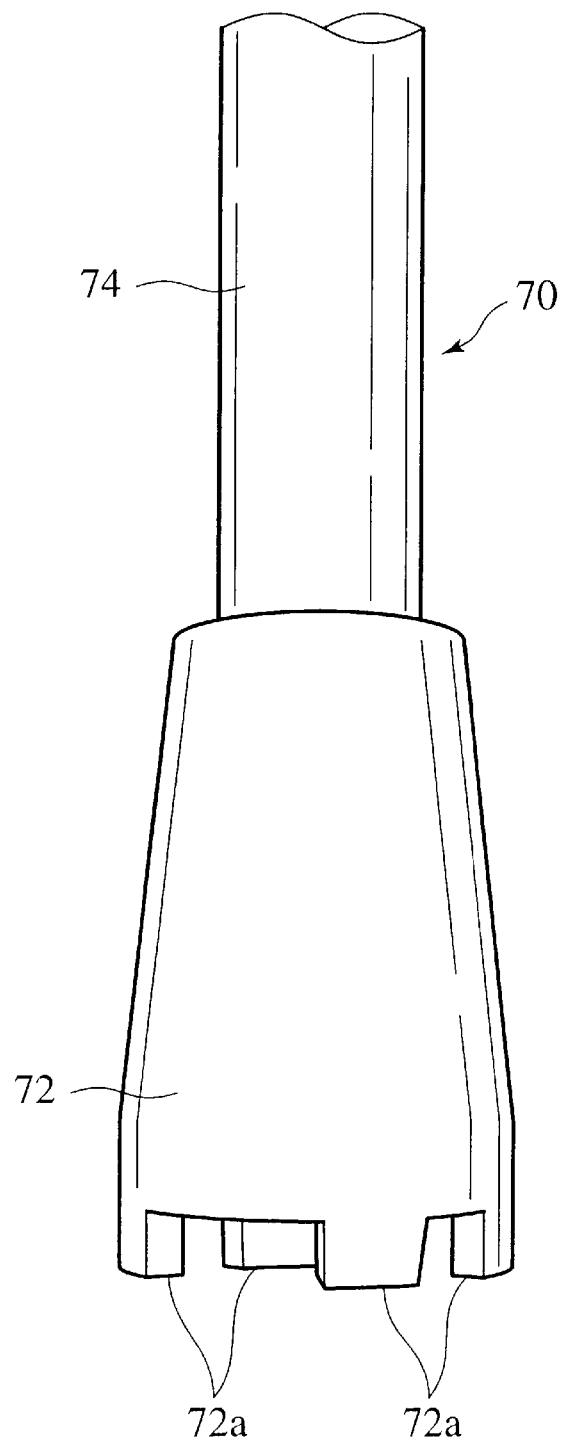
FIG. 12 is an enlarged, front view of a driver tool specifically suited for use in the nut member shown in FIG. 8.

In FIGS. 8 and 12, there is shown a fourth preferred embodiment of a driver tool 70 for rotating the nut member 52. The driver tool 70 includes a hollow, tubular tool end 72 and an elongated shaft 74 extending upward from the tubular body 72. A lower end of the tubular body has a plurality of substantially axially extending engaging segments 72a that are adapted to engage with the tool engagement grooves 56 formed on the upper wall of the nut member 52. The tubular body 72 is designed to have a diameter substantially equal to the nut member 52.

With such a structure discussed above, the anchoring screw sections 20 of the plural spinal implants 16 penetrates the vertebral bodies and, subsequently, the connecting rod 14 and the spherical engaging segment 14a are located in the rod retaining groove 54 of the implant body 18. In next step, the rod retaining member 60 is brought into engagement with the rod retaining groove 54 of the implant body 18, and the nut member 52 is screwed into the outer thread 50 of the implant body 18. The nut member 52 is rotated with the driver tool 70 of which engaging teeth 72a meshes with the tool engagement grooves 56 of the nut member 52, such that the nut member 52 is fixed in place. This movement is enhanced with the aid of the driver tool 70, providing ease of fixing operation of the nut member 52 to the implant body 18. As previously discussed, since the tubular body 72 has substantially the same diameter as the nut member 52 and an outer periphery of the tubular body 72 of the driver tool 70 does not interfere with an outer periphery of the adjacent retaining plug, thereby enhancing easy fixing operations of the driver tool 70 with respect to the adjacent retaining plugs located in a narrow space. The tool engagement grooves 56 may not be limited to the specific groove shown in FIGS. 8 and 9, but may have any other configuration such as a bore.

FIGS. 13 to 16 show a fifth preferred embodiment of a driver tool according to the present invention, with the spinal implant 16 being identical in structure with that of the first preferred embodiment except that the retaining plug 32 has a non-circular, hexagonal engagement groove 32A. In the fifth preferred embodiment, an upper end of a driver tool 78 has a grip section 78a, and a lower portion formed with a tool end 78b that has a hexagonal, nut engagement tip 78c. The driver tool 78 is used in combination with a nut guide 80 that includes a grip section 84 and a hollow, cylindrical shaft 82. The grip section 84 has an inner guide bore 84a that is adapted to receive the grip section 78a of the driver tool 78. The cylindrical shaft 82 has an axially extending through-bore 86 to guide the driver tool 78. A lower end of the cylindrical shaft 82 has an inner threaded bore 88, a nut guide chamber 90, an engaging guide chamber 92, and a rod engaging recess 94 that is adapted to receive the connecting rod 14. Plural preliminary mounting stems 98 are fixedly connected to a mounting base 96 for temporarily supporting respective nut members 32 on top ends of the stems. The nut members 32 have the hexagonal engagement grooves 32*a*, respectively.

Figure 13:
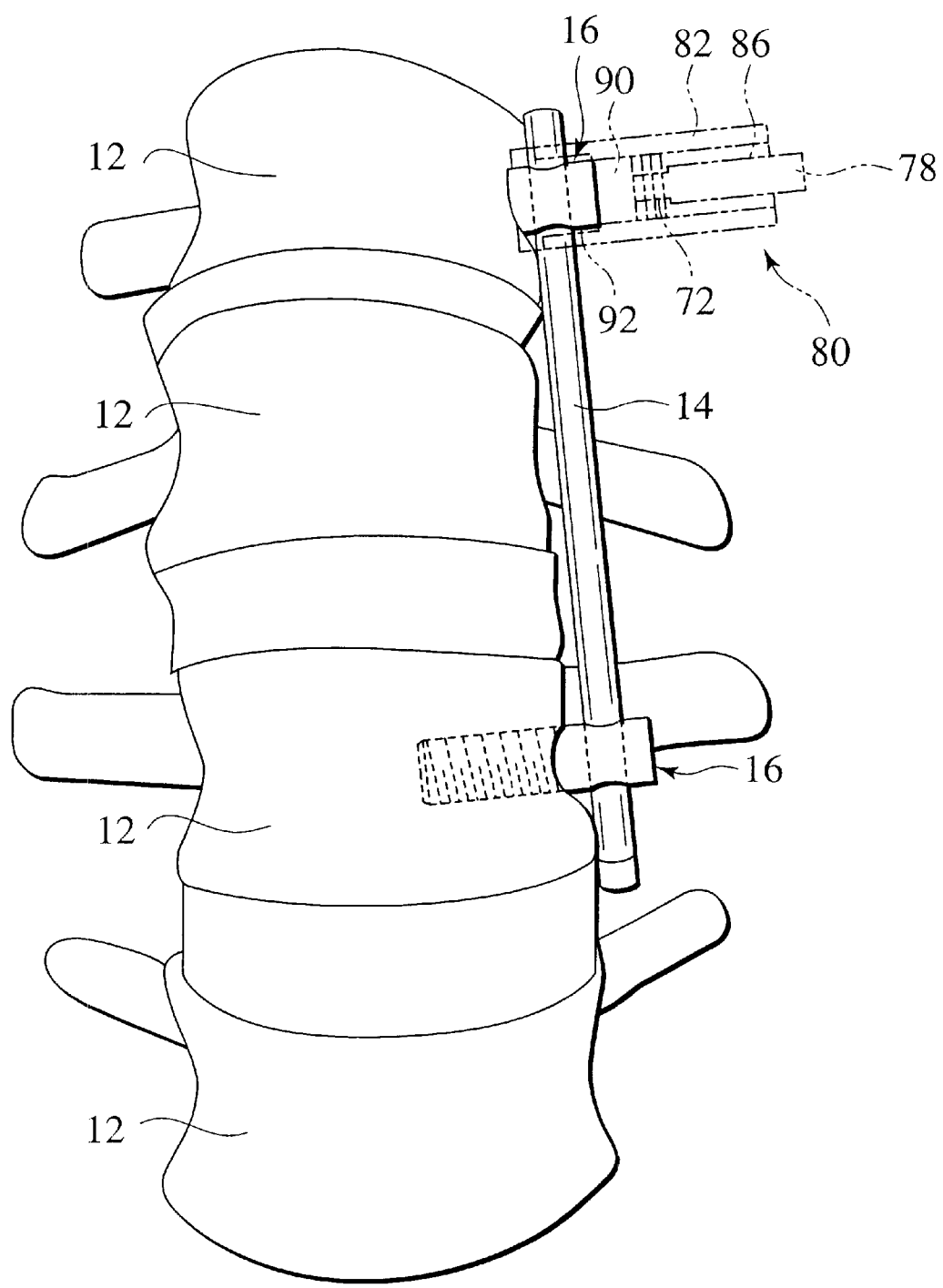
FIG. 13 is an enlarged view for illustrating the relationship between the spinal implant and a nut guide of a fourth preferred embodiment according to the present invention.
Figure 14:
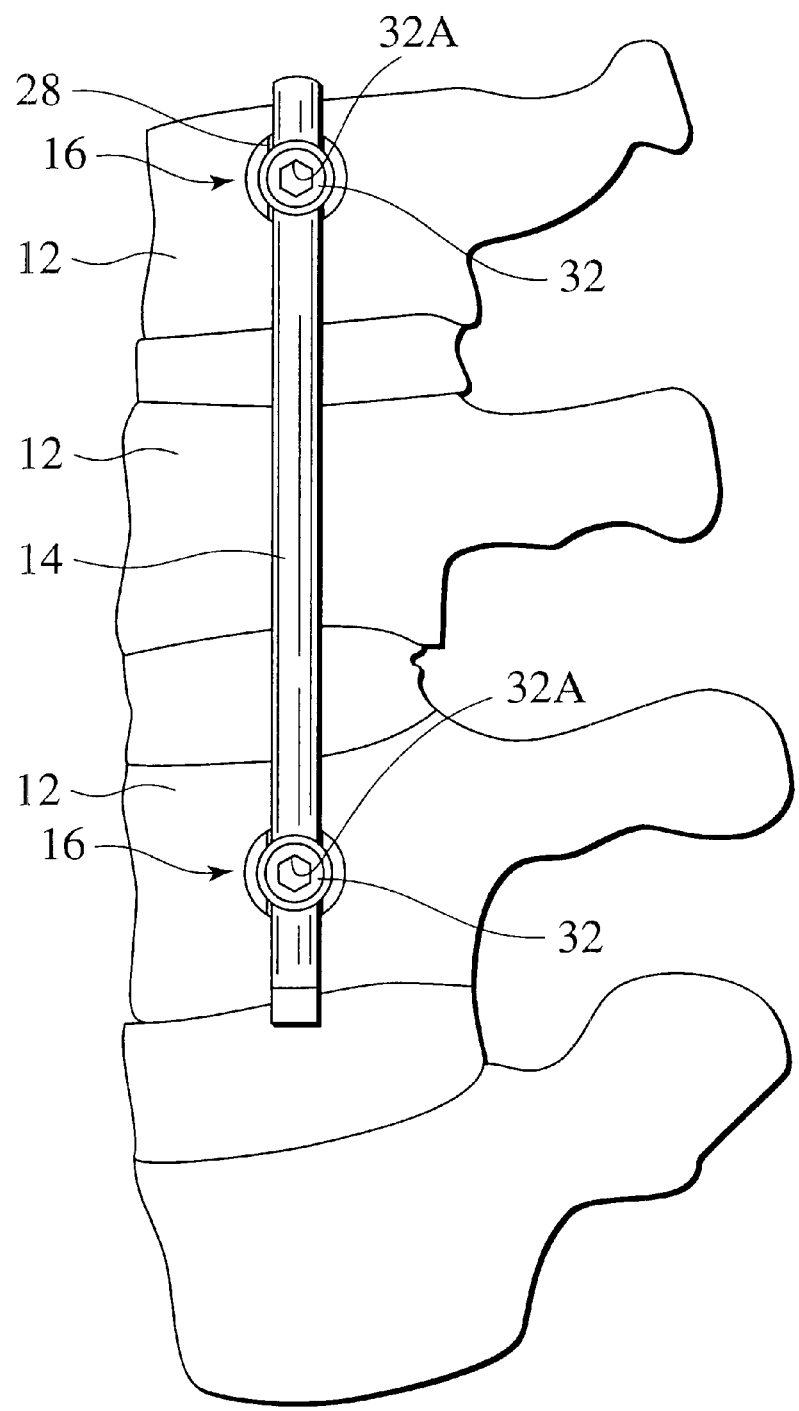
FIG. 14 is a side view of the osteosynthesis device shown in FIG. 13.
Figure 15:
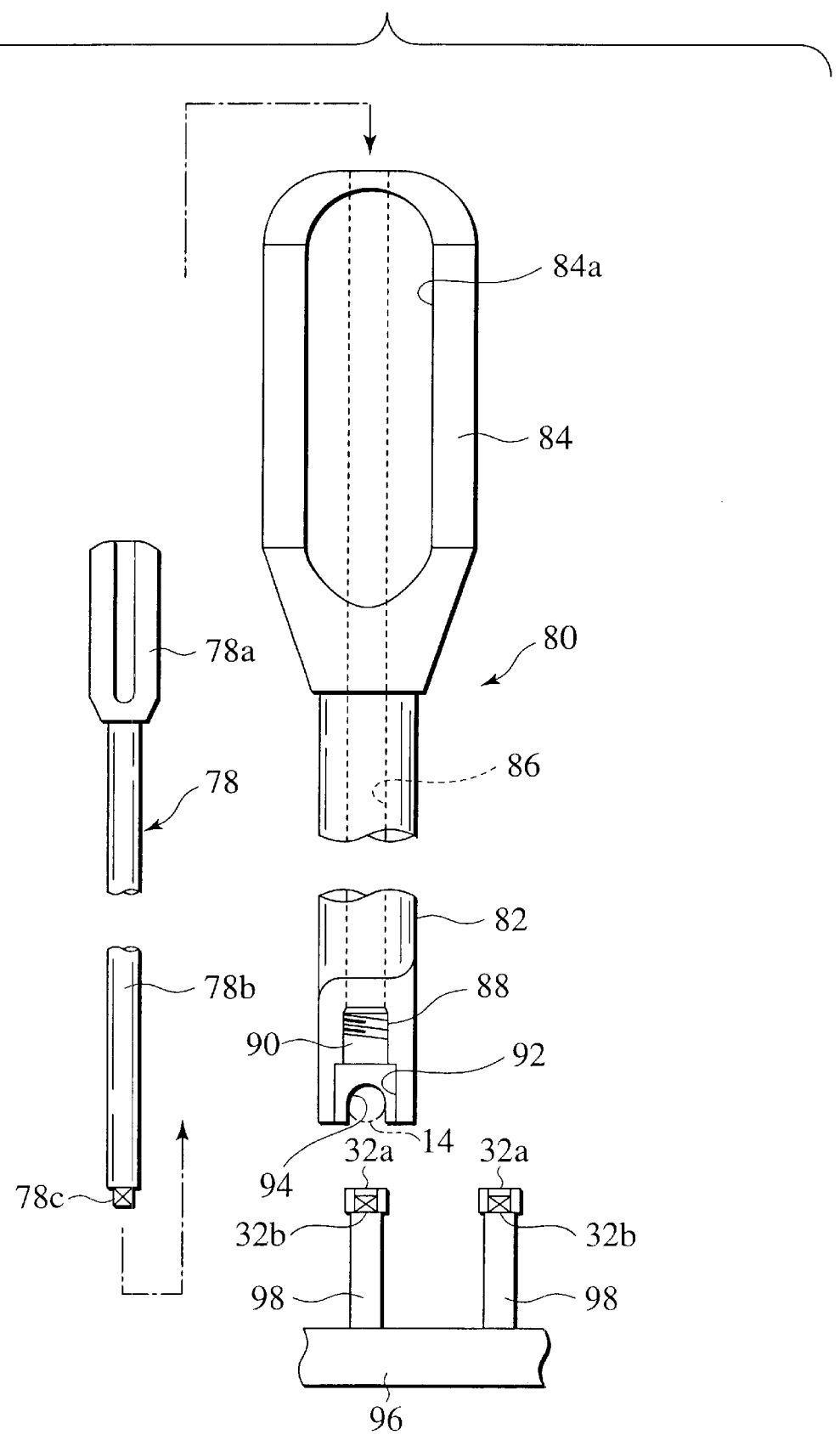
FIG. 15 is an enlarged, exploded view of the nut guide shown in FIG. 13.
Figure 16:
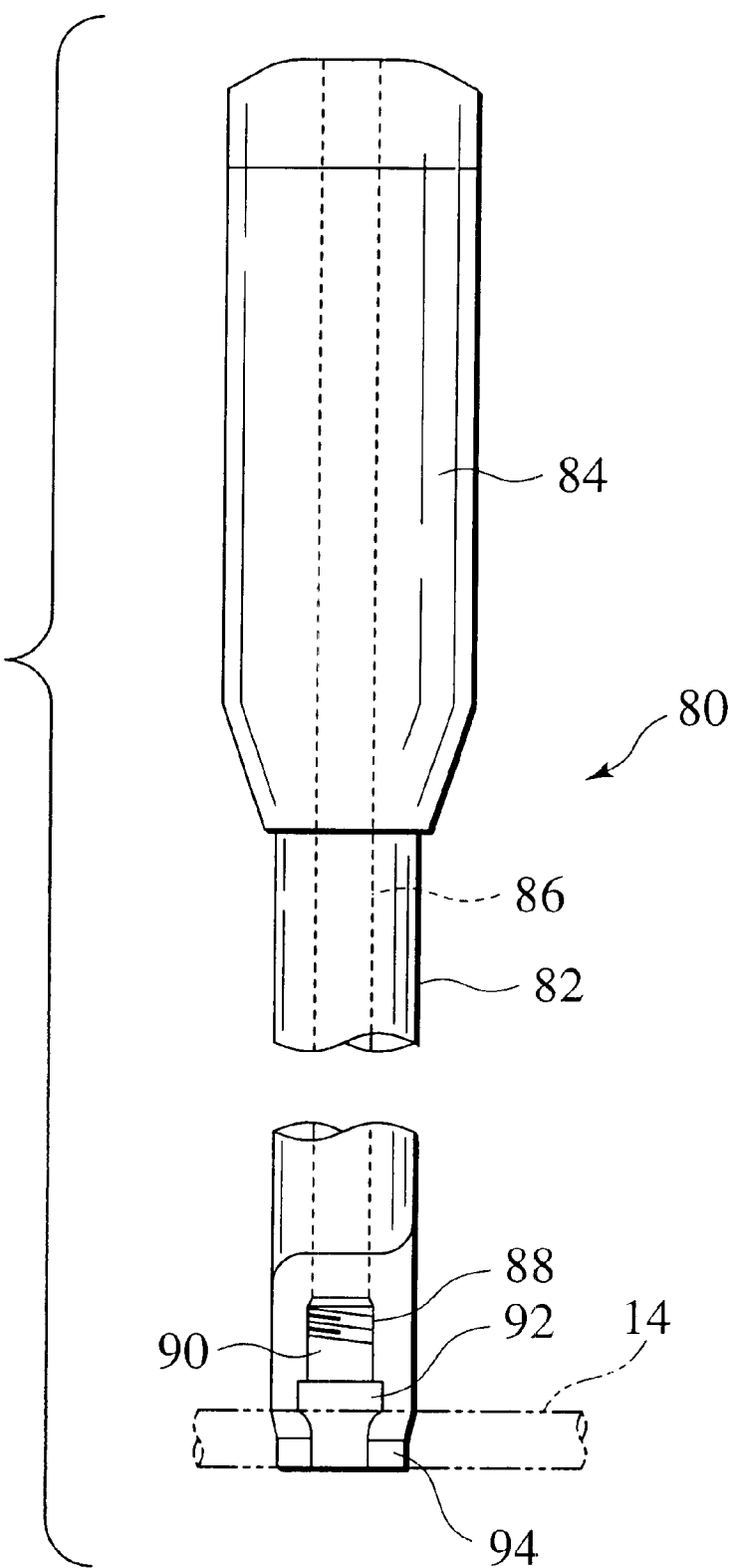
FIG. 16 is an enlarged side view of the nut guide shown in FIG. 13.

In operation, the plural spinal implants 16 are sequentially fixed into the vertebral bodies 12, and the connecting rod 14 is suitably located in the rod retaining recesses 28 of the implant 16. In a subsequent step, the nut guide 80 is placed on one of the nut members 32,which has been placed on the mounting stem 98, such that the nut member 32 is guided through the nut guide hole 90 of the nut guide 80. The nut member 32 is thud held with the nut guide 80, and the nut guide 80 is moved to an operating position shown in FIG. 13. In this event, the rod engaging recess 94 of the nut guide 80 is aligned with the connecting rod 14 such that the upper portion of the implant body 18 engages with the engaging guide bore 92 of the nut guide 80 in a manner as shown in FIG. 13. Then, the driver tool 78 is inserted through the nut guide 80 until the engagement tip 78*c* engages with the tool engagement groove 32*a* of the nut member 32, and the driver tool 78 is rotated to cause the nut member 32 to be screwed into the implant body 18 of the spinal implant 16 until the nut member 32 is brought into contact with the connecting rod 14. Accordingly, the nut member 32 is easily secured to the implant body 18 in a highly reliable manner without causing any misalignments or difficulties.

The spinal implant, the driver tool and the nut guide of the present invention provide numerous advantages over the prior art practices and which include:

(A) The spinal implant includes an implant body for retaining a vertebral connecting rod, and an anchoring screw section longitudinally extending from the implant body and adapted to be anchored in a vertebral body. The anchoring screw section has a plurality of spinal openings to permit borne ingrowth therein, with a resultant improved fixation of the spinal implant. Each of the spinal openings includes a longitudinally extending slit or laterally extending bore that thoroughly extends from one side to the other side.

(B) The anchoring thread section may also have a hollow, internal fusion chamber communicating with the spinal openings and longitudinally extending through the thread section to allow borne ingrowth therein. With this structure, the spinal implant can be anchored in the vertebral body with a suitable fixing condition in an early stage and, in a subsequent stage, the spinal implant can further be firmly anchored in the vertebral body owing to the borne ingrowth progressed in the spinal openings and the internal fusion chamber. This results in a reliable fixation of the spinal implant relative to the vertebral body for an extended time period.

(C) A head portion of the implant body has a rod member stabilizing means to retain the connecting rod relative to the adjacent spinal implants for adapting it to the differences in alignment between a rod retaining section and the connecting rod, the height of the rod retaining section, and angulation and depth of penetration of the anchoring screw sections. Thus, the connecting rod can be easily supported in place with the adjacent spinal implants without causing any complicated, troublesome alignments or adjustments of angulation and depth of penetration of the anchoring screw sections.

(D) The spinal implant also includes a nut member which is designed to be screwed into a head portion of the implant body, with the nut member including a rod retaining member for retaining the connecting rod in place in the implant body while permitting pivotal movement of the connecting rod, thereby preserving smooth mobility to compensate for positional misalignments or erroneous orientation between the adjacent spinal implants.

(E) A driver tool is employed to rotate the nut member relative to the implant body, with the driver tool having at least one engaging segment that engages with an engagement groove of the nut member and having substantially the same diameter as that of the nut member, enabling the driver tool to drive the nut member of one of the spinal implants in an easy manner without conflicting the adjacent nut member of the other spinal implant closely positioned to the former spinal implant.

(F) A nut guide is proposed for reliably guiding the nut member to be easily removed to the anchored spinal implant in a highly reliable manner, and a driver tool is also guided by the nut guide to cause an engaging tip of the driver tool to precisely engage with the engaging groove of the nut member of the spinal implant. Consequently, the nut member can be smoothly coupled to the implant body within a short time period without causing rotation of the implant body relative to the vertebral body.

The foregoing description of the preferred embodiments of the invention has been presented to illustrate the principles of the invention and not to limit the invention to the particular embodiments illustrated. For example, although the preferred embodiments have been illustrated and described that the anchoring screw section of the spinal implant includes a spinal opening composed of an elongated slip or plural laterally extending bores, the spinal opening may have any other suitable configurations such as an oblong opening or an elliptical bore. It is intended that the scope of the invention be defined by all of the embodiments encompassed within the following claims, and equivalents thereof.

What is claimed is:

1. A spinal implant for an osteosynthesis device having a vertebral connecting rod for interconnecting adjacent vertebral bodies, comprising:

an implant body including a head section having a threaded portion and a rod retaining recess opening outward for retaining the connecting rod therein and a slanted engagement surface formed on a bottom wall of the rod retaining recess therein, and an anchoring screw section longitudinally extending from the head section and adapted to be screwed into the vertebral body;

a nut member screwed to the threaded portion of the head section to maintain the connecting rod in place; and a rod movement stabilizing device directly located in at least one of the rod retaining recess and the nut member for allowing pivotal movement of the connecting rod in the retaining recess, thereby preserving mobility to the connecting rod.

2. A spinal implant according to claim 1, wherein the anchoring screw section has a plurality of spinal openings to permit borne ingrowth therein.

3. A spinal implant according to claim 2, wherein the anchoring screw section also has a hollow internal fusion chamber formed in an axial direction of the thread section and communicating with the spinal openings to permit borne ingrowth into the spinal chamber.

4. A spinal implant according to claim 2, wherein the spinal opening is formed in an elongated slit axially extending along an axis of the thread section.

5. A spinal implant according to claim 2, wherein the rod retaining recess has a U-shaped profile having a semicircular bottom wall, and wherein the rod movement stabilizing device includes the slanted engagement surface formed on the bottom wall of the rod retaining recess to permit pivotal movement of the connecting rod therein.

6. A spinal implant according to claim 4, wherein the anchoring screw section has a plurality of longitudinally extending thin wall portion to permit plastic deformation of the anchoring screw section.

7. A spinal implant according to claim 2, wherein the spinal openings are formed along the axis of the anchoring screw section in transverse direction thereof.

8. A spinal implant according to claim 1, wherein the head section has a threaded portion in close proximity to the retaining recess wherein the nut member is screwed onto the threaded portion of the head section, the nut member has an upper wall formed with a tool engagement groove adapted to engage with a driver tool.

9. A spinal implant according to claim 8, wherein the tool engagement groove includes a transverse groove laterally formed on the distal end of the nut member.

10. A spinal implant according to claim 9, wherein the connecting rod has a spherical engaging member adapted to be received in the retaining recess of the head section, with the spherical engaging member being retained in place with the nut member.

11. A spinal implant according to claim 10, wherein the head section includes a pair of arch-shaped upright segments adapted to engage with first parts of the spherical member, and the nut member includes a ring-shaped structure having a pair of arch-shaped engagement groove adapted to engage with second parts of the spherical member such that the head section of the implant body and the nut member permit pivotal movement of the spherical member, thereby preserving mobility to the connecting rod.

* * * * *